United States Patent [19]
Reeves

[11] Patent Number: 5,291,903
[45] Date of Patent: Mar. 8, 1994

[54] DISPOSABLE STERILE COVER AND RESTRAINT FOR SURGICAL ARM SUPPORT

[75] Inventor: Thomas C. Reeves, Birmingham, Ala.

[73] Assignee: Production Products, Inc., Homewood, Ala.

[21] Appl. No.: 7,824

[22] Filed: Jan. 22, 1993

Related U.S. Application Data

[63] Continuation of Ser. No. 711,859, Jun. 7, 1991, abandoned.

[51] Int. Cl.$^5$ .............................................. A61F 5/04
[52] U.S. Cl. .................................. 128/878; 128/877; 128/845; 128/DIG. 15
[58] Field of Search .............. 128/845, 846, 849, 853, 128/856, 869, 872, 878, 877, DIG. 15

[56] References Cited

U.S. PATENT DOCUMENTS

| | | | |
|---|---|---|---|
| 1,183,225 | 5/1916 | Overmeyer | 128/878 |
| 2,693,794 | 11/1954 | Neville | 128/878 X |
| 3,196,870 | 7/1965 | Sprecher et al. | 128/DIG. 15 X |
| 3,640,273 | 2/1972 | Ray | 128/878 X |
| 3,824,998 | 7/1974 | Snyder | 128/856 X |
| 3,934,582 | 1/1976 | Gorrie | 128/856 X |
| 4,036,220 | 7/1977 | Bellasalma | 128/856 X |
| 4,253,451 | 3/1981 | Soloman | 128/856 X |
| 4,286,588 | 9/1981 | Lovegrove | 128/DIG. 15 X |
| 4,308,864 | 1/1982 | Small et al. | 128/856 |
| 4,375,809 | 3/1983 | Meals | 128/845 X |
| 4,945,925 | 8/1990 | Garcia | 128/828 X |

FOREIGN PATENT DOCUMENTS

| | | | |
|---|---|---|---|
| 877507 | 12/1942 | France | 128/846 |
| 89/10103 | 11/1989 | PCT Int'l Appl. | 128/878 |

*Primary Examiner*—Rober A. Hafer
*Assistant Examiner*—Sam Rimell
*Attorney, Agent, or Firm*—Veal & Associates

[57] ABSTRACT

An arm support cover including a sheath having an impermeable inner layer and an absorbent outer layer. The sheath is elongated and has an opening at a selected end thereof for insertion therethrough of a surgical arm support commonly used to support and secure a patient's arm during surgery so that intravascular and intramuscular hypodermics inserted within the patient's arm will not be inadvertently disturbed during the operation. Two pair of straps each including a first strap having a hooked portion and a second strap having a looped portion, are connected to the underside of the sheath. In operation, the first and second straps are wrapped in opposite direction around the sheath, support arm and patient's arm with the hook and loop portions being engaged to connect the strap and secure the patient's arm. An alternate embodiment includes a pair of straps each having a hooked portion and looped portion of hook-and-loop connector on opposite sides thereof. The straps are connected to the underside of the sheath in longitudinally spaced relation thereon. The straps are wrapped around the sheath, the arm support received therein and over the patient's arm. The hooked portion is pressed against and engages the looped portion to secure the patient's arm to the arm support with the sheath therebetween.

6 Claims, 3 Drawing Sheets

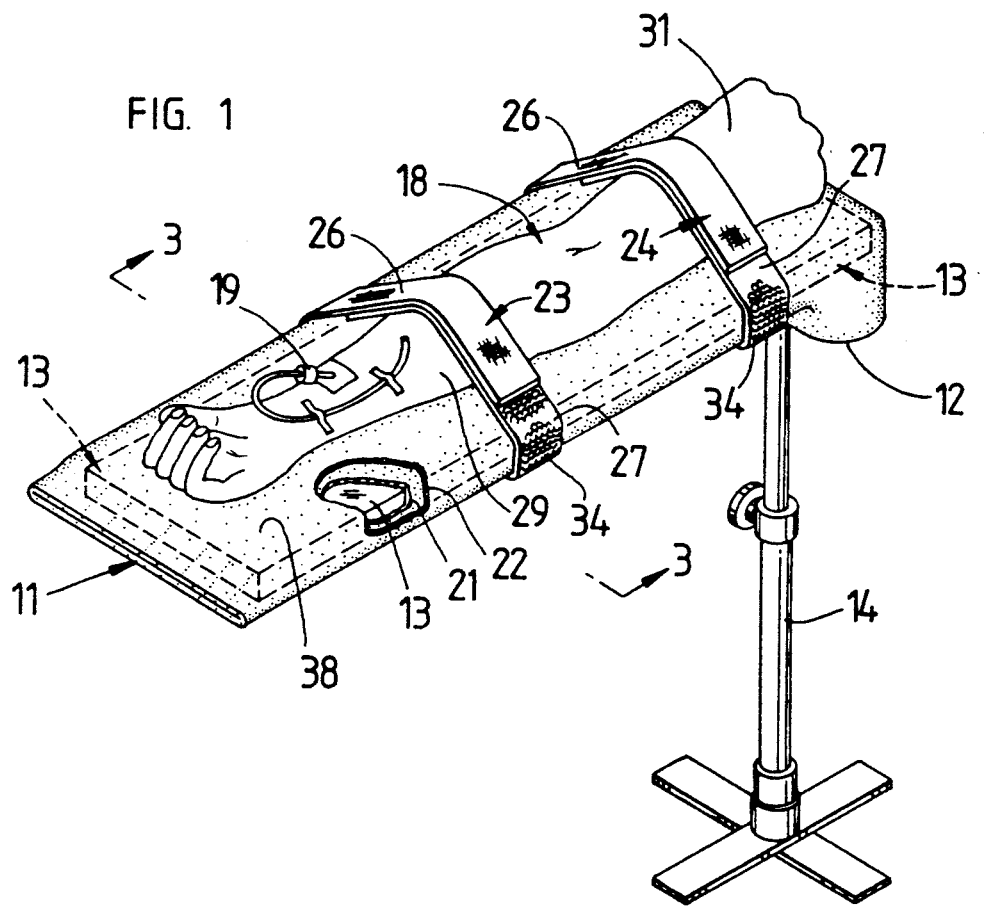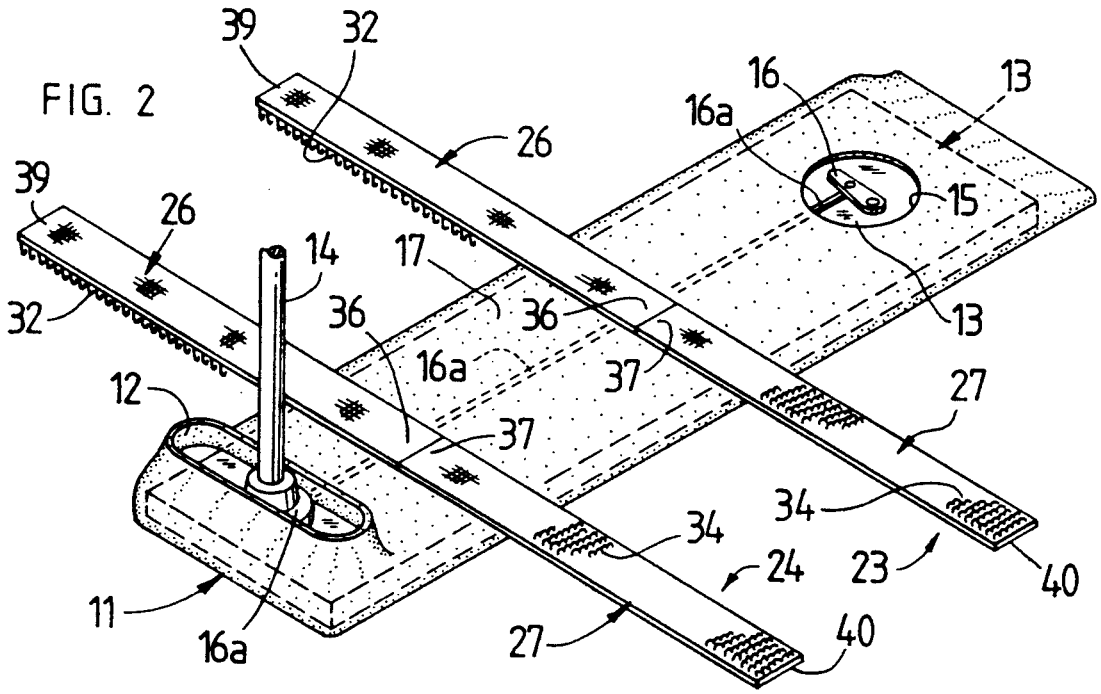

DISPOSABLE STERILE COVER AND RESTRAINT FOR SURGICAL ARM SUPPORT

This is a continuation of application Ser. No. 07/711,859, filed Jun. 7, 1991, now abandoned.

FIELD OF THE INVENTION

The present invention relates to disposable medical coverings for isolating permanent patient support fixtures from body fluids and tissue discharged or removed from the patient during medical operations. More particularly, the present invention relates to surgical arm support coverings having restraining apparatus thereon for securing the patient's arm to a bedside arm support.

BACKGROUND OF THE INVENTION

During selected medical operations, various hypodermics such as intravascular needles and/or catheter may be introduced into the patient's arm to supply fluids, anesthetic or probes to selected regions of the body. To facilitate proper insertion of these hypodermics and to prevent inadvertent removal thereof by the patient or the operating room staff, obstetrical operating room table arm supports are positioned adjacent the operating table on which the patient is supported. Towels are placed over the arm support to absorb any blood from the patient's arm. The patient's arm is typically secured to the arm support by wrapping adhesive tape around the patient's arm, the towels, and the arm support. This method, though effective to secure the patient's arm, requires that the tape be forceably removed from the patient's arm. This can be a painful experience for the patient and may damage the skin of patient's arm. Removal of the tape leaves unsightly and unsanitary adhesive residue on the bedside support and the patient's arm. The towels may absorb blood or other body fluids discharged thereon, but do not prevent such body fluids from contacting the bedside support. Therefore, after each operation the bedside support must be thoroughly cleaned to remove adhesive residue and contaminating body fluid.

SUMMARY OF THE INVENTION

It is the principal object of the present invention to provide a disposable covering for bedside arm supports.

In support of the principal object, another object of the present invention is to provide an arm support cover that absorbs body fluids discharged from a patient's arm while isolating the arm support from such body fluids.

Yet another object of the present invention is to provide a disposable obstetrical or operating room arm support cover having disposable restraining apparatus connected thereto that does not require the use of adhesive tape.

A further object of the present invention is to provide a disposable arm support cover with the characteristics cited above having restraining means that completely encircles the arm support, the cover and the patient's arm.

These and other advantages of my invention are accomplished through the use of an elongated sheath having an opening in one end thereof through which the bedside arm support is received. The sheath has an impermeable inner layer, for isolating the arm support from bodily fluids, and may have an absorbent outer layer integrally connected to the inner layer for absorbing such bodily fluids. A first pair of straps are affixed to one another and an underside portion of the sheath at one end thereof for securing the patient's forearm to the arm support. A second pair of straps are connected to one another and the underside portion in spaced relation to the first pair for securing the patient's upper arm to the arm support. Each pair comprises a first strap constructed of the hooked portion of a hook-and-loop connector and a second strap constructed of the looped portion of hook-and-loop connector. To secure the patient's arm, the first and second strap are wrapped in opposite directions around the sheath and over the patient's arm. The straps are detachably connected at the free ends thereof to secure the patient's arm to the sheath and arm support.

An alternate embodiment includes a pair of separate straps each connected to the sheath much the same as the pairs of straps previously described. Each strap has a hooked portion on one side and a looped portion on the other. The strap is wrapped over the patient's arm and around the sheath with the looped portion being pressed against and engaged by the hooked portion to secure the patient's arm to the sheath and arm support. After the operation is complete, the straps are disengaged, the patient's arm is removed from the arm support and the sheath and attached straps are disposed of.

BRIEF DESCRIPTION OF THE DRAWINGS

Apparatus embodying features of my invention are depicted in the accompanying drawings which form a portion of this disclosure and wherein:

FIG. 1 is a perspective view of a first embodiment of the present invention supported by an arm support and engaging a patient's arm;

FIG. 2 is a bottom perspective view of a first embodiment of the present invention partially broken to show the outer and inner layers thereof;

DESCRIPTION OF A PREFERRED EMBODIMENT

Figure 3:
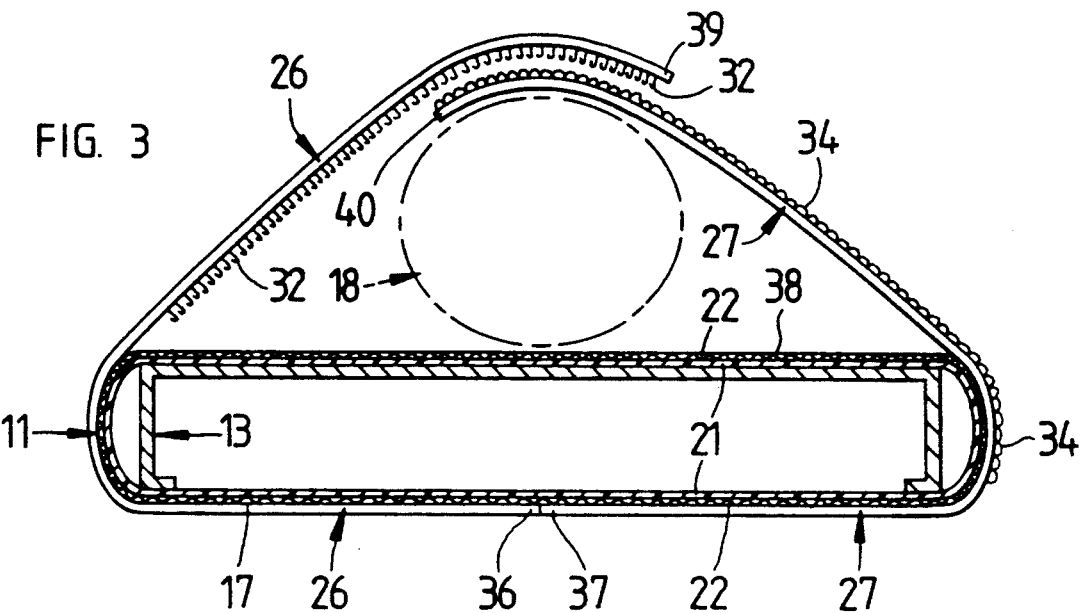
FIG. 3 is a section view 3—3 of FIG. 1.

Referring to the drawings for a clearer understanding of the invention, it should be noted that the present invention contemplates the use of a flexible sheath 11. The sheath is elongated and has an opening 12 on one end thereof through which a bedside arm support 13 is received. The arm support 13 is supported on an arm support stand 14. A hole 15 is defined in an underside portion 17 of the sheath 11 and proximate an end thereof opposite the opening 12. The hole 15 provides access to a lever 16 which is operatively connected to a stand engaging mechanism 16a. The stand engaging member 16a, which is commonly known in the industry, selectively grips the stand 14 to secure the arm support 13 to the stand 14 in non-rotating relation thereto. The lever 16, when moved to a first portion, urges the stand engaging mechanism 16a to a non-gripping position whereby the arm support 13 can be freely rotated relative to the stand 14.

The primary purpose of the arm support 13 is to hold the patient's arm 18 away from an operating table (not shown) during a medical operation. Selected intravascular and intramuscular hypodermics 19 are typically inserted in the patient's arm 18 prior to and during the operation and the support facilitates their insertion and use.

The patient's arm should be held as far from the operating table as possible to minimize inadvertent contact thereof by the operating staff. Blood, sweat or other body fluids (not shown) from the patient's arm 18 should be isolated from the arm support 13 to maintain a sanitary operating environment.

As is shown in FIG. 1, the sheath 11 includes an impermeable layer 21 for isolating the arm support 13 from body fluids from a patient's arm 18. An absorbent layer 22 may be integrally connected to the impermeable layer 21 for absorbing discharged body fluids. The sheath 11 is disposable and is removed after the operation and replaced with a new sheath of like construction.

As is shown in FIGS. 1-3, a first embodiment of the present invention includes the sheath 11 previously described having first and second pairs 23 and 24 of first and second straps 26 and 27. The first and second pairs 23 and 24 are spaced on the sheath 11 to engage a forearm portion 29 and upper arm portion 31 of the patient's arm 18 against an outer surface 30 of sheath 11, respectively. The first straps 26 include a hooked portion 32 of hook-and-loop connector, commonly known as Velcro, connected to a selected side thereof. The second straps 27 have a looped portion 34 of hook-and-loop connector connected to a selected side thereof. Each first strap 26 of each pair 23 and 24 is connected at a secured end 36 to a secured end 37 of the corresponding second strap 27. The secured ends 36 and 37 are connected to the underside portion 17.

In operation, the patient's arm 18 is placed on an upper portion 38 of the outer surface 30 of sheath 11. The first and second straps 26 and 27 are wrapped in opposite directions around the sheath 11 and arm support 13 and are detachably connected at free ends 39 and 40 by the corresponding hooked portions 32 and looped portions 34. The sheath 11 is fragile relative to the straps and, due to its disposable nature, may be susceptible to tearing. Accordingly, the straps 26 and 27 by being joined at their secured ends 36 and 37 encircle the sheath and arm and minimize the exertion of force on the sheath by movement of the patient's arm 18. The detachable nature of the hook-and-loop connector permits attachment of the arm 18 to the arm support without the use of adhesive. The patient's arm is released from the arm support 13 by detaching the hooked and looped portions 32 and 34. The sheath 11 is also freely detachable from the arm support 13 once the straps are disengaged. Hook-and-loop connector is relatively inexpensive and is easily destroyed by incineration, making the straps especially suitable for disposable use.

Figure 5:
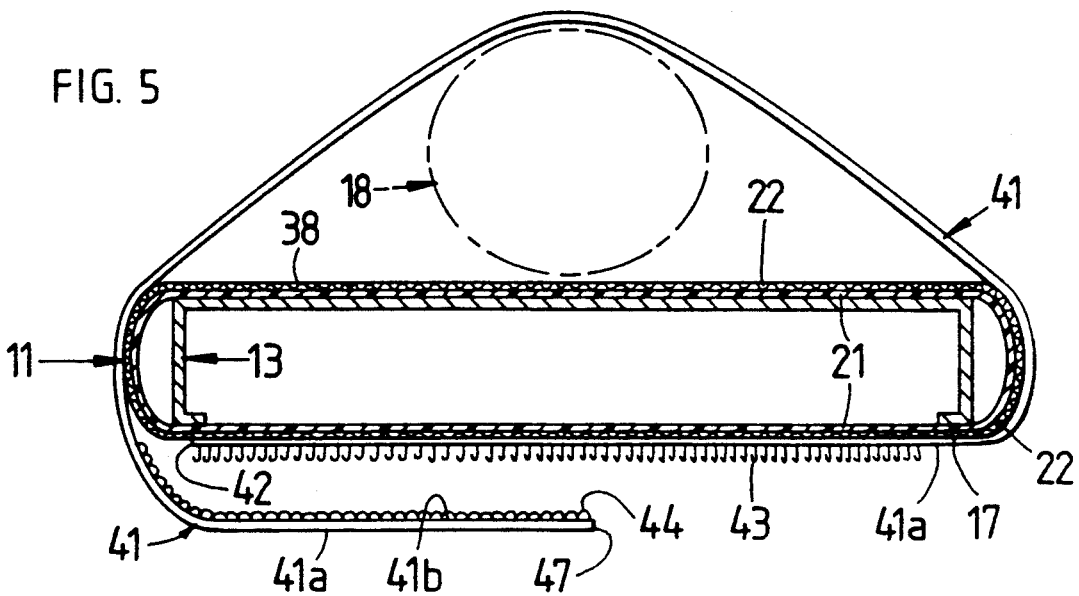
FIG. 5 is a sectional view taken along line 5—5 of FIG. 4.
Figure 4:
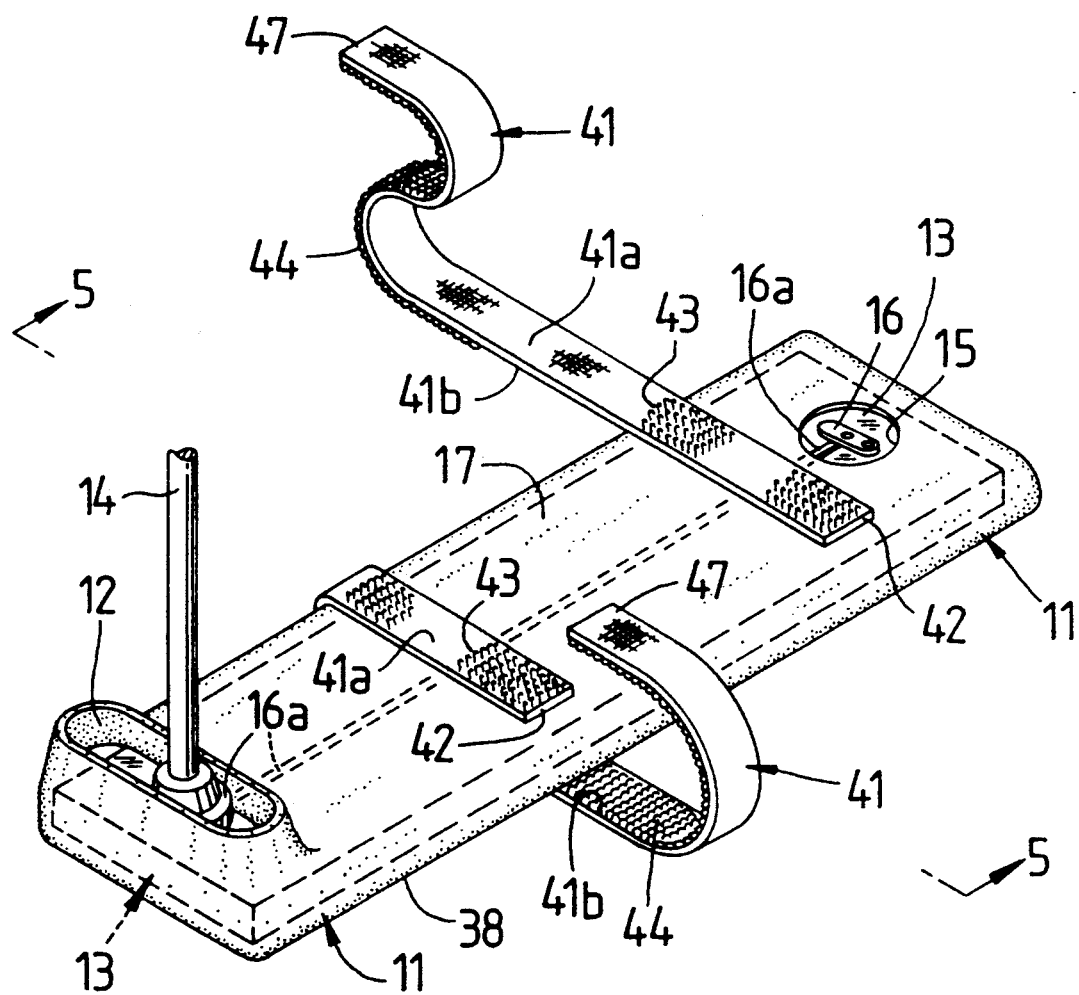
FIG. 4 is a bottom perspective view of a second embodiment of the present invention.

As is shown in FIG. 4, a second embodiment of the present invention includes the sheath 11 previously described and a pair of straps 41 having secured ends 42 affixed to the underside portion 17 of sheath 11. The straps 41 are spaced apart on the sheath 11 to engage the forearm portion 29 and upper arm portion 31 of the patient's arm 18. As shown in FIGS. 4 and 5, each strap 41 includes a hooked portion 43 of hook-and-loop connector connected to a selected side 41a of strap 41. A looped portion 44 of hook-and-loop connector is connected to an opposite side 41b of the strap 41 and when engaged by the hooked portion 43 is detachably connected thereto to hold the strap in place.

In operation, the patient's arm 18 is placed on the upperside portion 38 of the sheath 11. The straps 41 are wrapped over the patient's arm 18 and around the sheath 11 with the looped portion 43 at a free end 47 of each strap 41 being detachably connected to the hooked portion 44 to secure the patient's arm to the sheath 11 and the arm support 13. The sheath 11 is relatively fragile and may be susceptible to tearing due to its disposable nature; however, the straps 41 by being completely wrapped around the arm support 13 and detachably connected at free and secured ends 47 and 42, provide securing means that minimize the exertion of force on the sheath 11 by movement of the patient's arm 18. Detachment and disposal of the second embodiment is similar to that described in the first embodiment. From the foregoing, it should be clear that the present article represents a substantial improvement in support arm coverings by providing a disposable covering having disposable arm retaining means connected thereto.

While I have shown my invention in two forms, it will be obvious to those skilled in the art that it is not so limited but is susceptible of various changes and modifications without departing from the spirit thereof.

What I claim is:

1. A disposable arm support cover for securing a patient's arm to a surgical arm supporting device during surgery and for isolating said arm support device from body fluids discharged from said patient's arm, said disposable arm support cover comprising:
   (a) an elongated frangible disposable sheath which envelops an associated surgical arm supporting device, said sheath having an impermeable layer of material, an outer absorbent layer of material and an opening at one end thereof for insertion therein of said arm supporting device; and
   (b) at least two straps connected to and spaced along an underside of said sheath and disposable therewith for securing said patient's arm against said outer absorbent layer of said sheath and to said arm supporting device without leaving an unsanitary adhesive residue on said patient's arm or said arm supporting device, wherein each of said straps comprises: a hooked portion of a hook-and-loop connector connected to a selected side of each of said straps; and a looped portion of said hook-and-loop connector connected to a side opposite said selected side of each of said straps, wherein each of said straps is wrapped completely around said arm supporting device, said patient's arm and said sheath with said hooked portion being applied and detachable connected to said looped portion to secure said patient's arm to said arm supporting device.

2. A disposable arm support cover as defined in claim 1 wherein said hooked portion coextends the entire length of each of said straps on said selected side thereof and said looped portion coextends the entire length of each of said straps on said opposite side thereof.

3. A disposable arm support cover as defined in claim 2 wherein said straps comprise a first and second strap, said first strap connected to said sheath proximate a predetermined end thereof for securing a forearm portion of said patient's arm, said second strap connected to said sheath in longitudinally spaced relation to said first strap for securing an upper arm portion of said patient's arm.

4. A disposable article for covering a surgical arm supporting device and for securing a patient's arm to said arm supporting device and for isolating said arm supporting device from body fluids discharged from said patient's arm, said disposable article comprising:
  (a) an elongated disposable frangible sheath which envelops an associated surgical arm supporting device, said sheath having an impermeable layer of material, an outer absorbent layer of material and an opening at one end thereof for insertion therein of said arm supporting device; and
  (b) at least two pairs of straps connected to and spaced along an underside of said sheath and disposable therewith for securing said patient's arm to said arm supporting device with said sheath therebetween, wherein each said pair of straps comprises: a first strap constructed from a hooked portion of a hook-and-loop connector; and a second strap constructed from a looped portion of said hook-and-loop connector, wherein said first and second straps are wrapped in opposite directions around said sheath and over said patient's arm and are detachable and reattachable engaged to secure said patient's arm to said arm supporting device with said sheath therebetween.

5. A disposable article as defined in claim 4 wherein said first strap is affixed to said underside of said sheath and to a secured end of said corresponding second strap.

6. A disposable article as defined in claim 5 wherein a first pair of said pairs of straps is connected to said sheath proximate a predetermined end thereof for securing a forearm portion of said patient's arm and wherein a second pair of said pairs of straps is connected to said sheath in longitudinally spaced relation to said first pair for securing an upper arm portion of said patient's arm.

* * * * *